United States Patent [19]

Matsson et al.

[11] Patent Number: 5,525,304

[45] Date of Patent: Jun. 11, 1996

[54] APPARATUS FOR AUTOMATED CHEMICAL ANALYSIS WITH VARIABLE REAGENTS

[75] Inventors: Per Matsson, Excelsior; Armer Willenbring, Minnetonka; Michael Moreau, Andover, all of Minn.

[73] Assignee: Pasteur Sanofi Diagnostics, Paris, France

[21] Appl. No.: 265,189

[22] Filed: Jun. 24, 1994

[51] Int. Cl.⁶ ................................................. G01N 37/00
[52] U.S. Cl. .......................... 422/104; 422/63; 422/65; 422/102; 436/43; 436/180; 211/74; 211/89
[58] Field of Search .......................... 422/100, 99, 102, 422/63, 64, 65, 104; 436/43, 47, 49, 180, 807, 810; 211/74, 89; 206/446, 569

[56] References Cited

U.S. PATENT DOCUMENTS

| | | |
|---|---|---|
| 3,605,829 | 9/1971 | Genese et al. |
| 3,617,222 | 11/1971 | Matte . |
| 3,680,967 | 8/1972 | Engelhardt . |
| 3,684,453 | 8/1972 | Lartigue et al. ...................... 422/102 |
| 3,713,771 | 1/1973 | Taylor et al. . |
| 3,964,867 | 6/1976 | Berry . |
| 4,056,361 | 11/1977 | Peters et al. . |
| 4,517,851 | 5/1985 | Tice ...................................... 73/864.91 |
| 4,534,465 | 8/1985 | Rothermel et al. ................... 206/443 |
| 4,795,710 | 1/1989 | Muszak et al. . |
| 4,853,188 | 8/1989 | Toya ..................................... 422/104 |
| 4,944,924 | 7/1990 | Mawhirt et al. . |
| 5,137,693 | 8/1992 | Mawhirt . |
| 5,145,646 | 9/1992 | Tyranski ............................... 422/102 |
| 5,186,339 | 2/1993 | Heissler . |
| 5,322,668 | 6/1994 | Tomasso .............................. 422/104 |
| 5,350,564 | 9/1994 | Mazza et al. ........................ 422/63 |
| 5,378,433 | 1/1995 | Duckett et al. ...................... 422/100 |

FOREIGN PATENT DOCUMENTS 9322686  11/1993  WIPO .

Primary Examiner—James C. Housel
Assistant Examiner—Long V. Le
Attorney, Agent, or Firm—Fredrikson & Byron

[57] ABSTRACT

The invention provides a reagent supply system including a reagent rack for retaining a plurality of vials. The rack has a base and first and second walls extend upwardly from the base. The first wall includes an abutment extending toward the second wall and adapted to engage a first recess on one of the vials, while the second wall includes a flexible clip having a shoulder thereon, the shoulder being biased toward a position adapted to engage a second recess on the vial. The invention also provides a method of handling reagents which includes providing a variable reagent rack adapted to retain a plurality of vials and a common reagent pack containing a plurality of predetermined common reagents adapted to coact with reagents in the vials. A patient fluid is provided and a plurality of assays to be performed on that fluid are determined. Vials are then selected, each vial containing a different assay-specific reagent necessary for one of the assays, and the selected vials are loaded onto the rack. A quantity of reagent from one the vials and a quantity of a common reagent from the common reagent pack are transferred into a reaction vessel. A quantity of reagent from a second vial and a quantity of the common reagent are transferred into a second reaction vessel.

15 Claims, 6 Drawing Sheets

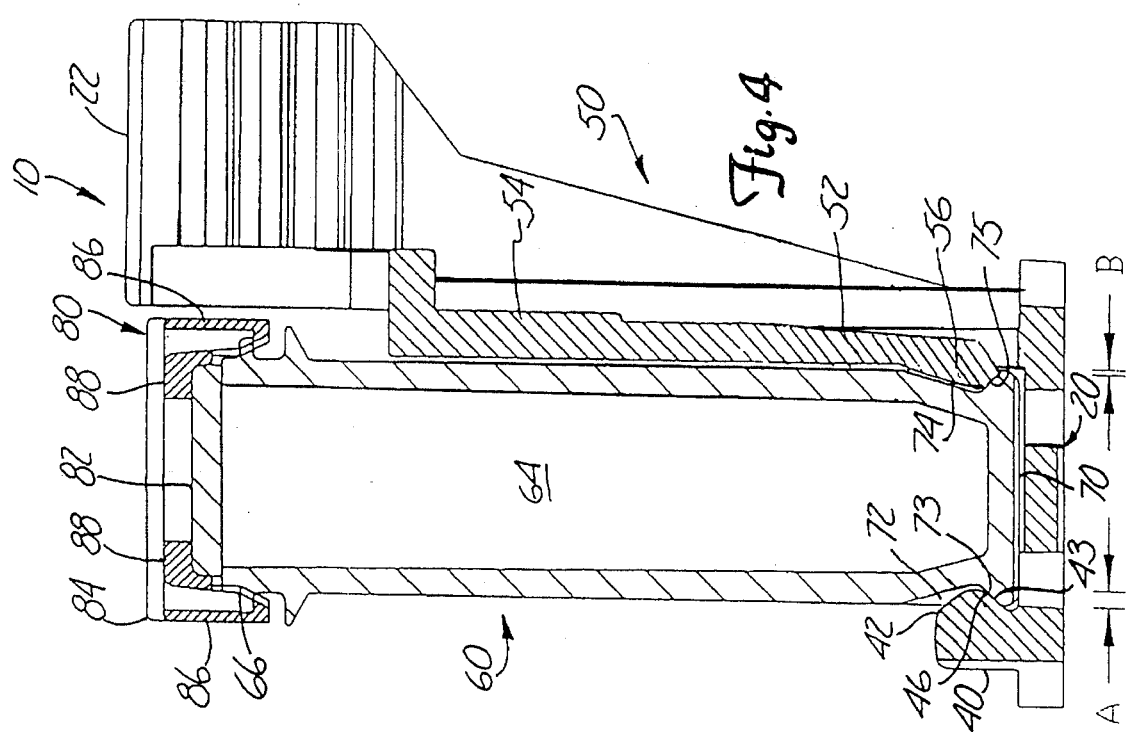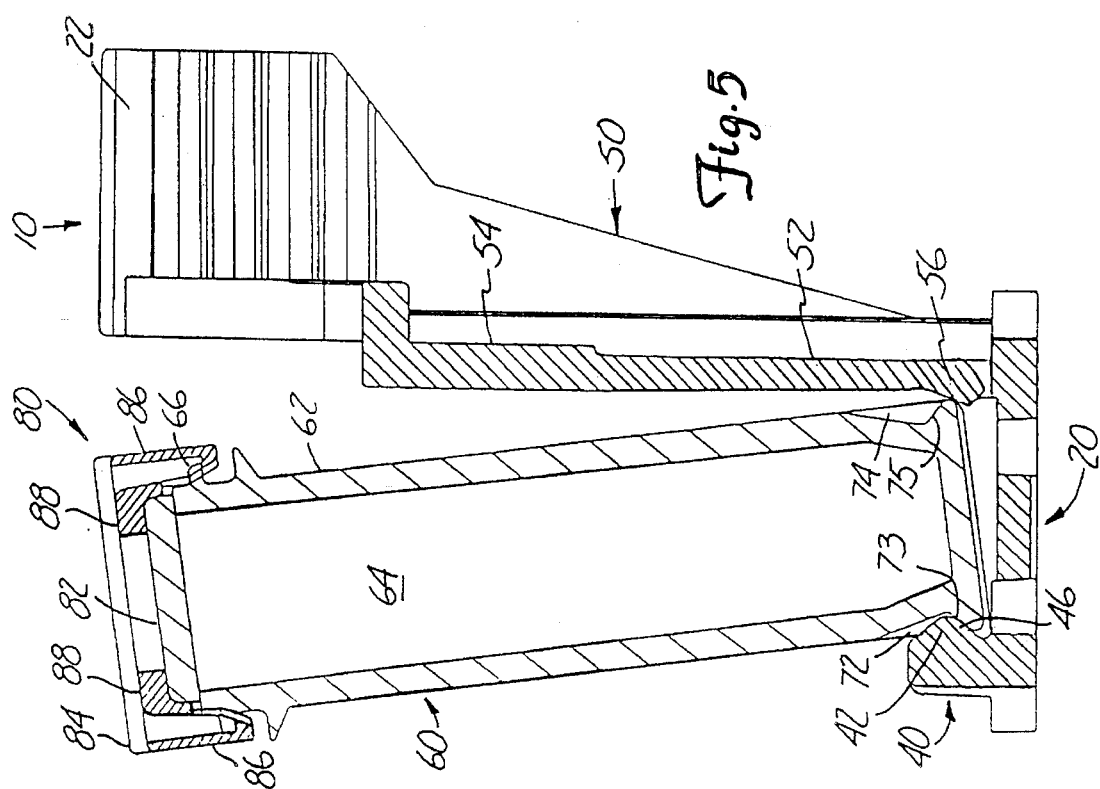

APPARATUS FOR AUTOMATED CHEMICAL ANALYSIS WITH VARIABLE REAGENTS

FIELD OF THE INVENTION

The present invention generally relates to automated chemical analysis and has particular application in automated testing of samples using variable reagents.

BACKGROUND OF THE INVENTION

Automated chemical analyzers are used to test samples of some fluids or other substances for the presence or absence of certain compounds or other chemical agents. For example, automated analyzers are frequently used to test a sample of a fluid from a patient (e.g. a blood or urine sample) for the presence of certain antibodies. In many instances, the test is for a specific antibody and a standard test using a predefined series of reagents is employed. In other instances, though, it may be desirable to be able to perform a series of tests for a variety of antibodies on a single sample.

Reagents for these automated tests are commonly provided in a pack of reagents, with each reagent pack having all of the reagents necessary for conducting a specific test. If the number of assays which can be performed is relatively limited, this can work well in an automated system. However, space for storing the reagent packs, which frequently must be refrigerated to maintain the viability of the reagents, in the analyzer is frequently at a premium due to the desire to keep the size of such analyzers to a minimum.

In many instances, a series of assays will have one or more reagents in common. One could include that same reagent with each reagent pack for such assays, but that would tend to take up needless space in the analyzer. However, in some cases, the assays tend to share most of the reagents in common and only one reagent solution need vary between different assays. For example, in allergy assays used to determine whether certain allergen antibodies are present in a sample, much of the reagents will remain the same from one allergen assay to the next, with only the specific allergen being tested varying between the tests.

As the number of reagent packs which can be stored in the analyzer is usually limited due to space constraints, providing a separate reagent pack for each allergen takes up a great deal of space and makes testing a sample for a series of allergens inconvenient and reduces the variety of other assays requiring different reagents which can take place at the same time, affecting the throughput of the analyzer.

SUMMARY OF THE INVENTION

The present invention provides a reagent supply apparatus and method for use in connection with an automated analyzer to simplify a variety of assays by storing a wider range of reagents on the analyzer at one time. One embodiment of the reagent supply apparatus of this invention provides a variable reagent rack having a series of interchangeable vials thereon to provide a plurality of assay-specific reagents on a single reagent pack. The variable reagent rack desirably has a plurality of vial-retaining clips for positioning and retaining vials of specific reagents on the pack, permitting an operator to vary the reagents on the pack by exchanging the vials on the rack with vials containing different reagents.

In a preferred embodiment, both the rack and the clips have an inwardly extending shoulder and the vials are provided with recesses for receiving those shoulders. The clips are formed of a resilient material and are biased inwardly to retain vials, but each clip can be urged out of engagement with the recess of a vial to permit removal of the vial from the reagent pack.

In an apparatus in accordance with a further embodiment of the invention, a reagent station includes at least one common reagent pack storing a predetermined quantity of a series of common reagents and a variable reagent rack as described above. Both the variable reagent rack and the common reagent pack are contained on a reagent supply platform, which may comprise a refrigerated carousel having slots for retaining the supplies of reagents.

In a method of the invention, an operator determines the assays required for a particular patient sample. The operator then loads a series of assay-specific reagent vials onto a variable reagent rack to provide assay-specific reagents necessary for each of a plurality of the assays required for the patient sample. The operator then loads the variable reagent rack and a common reagent pack onto the analyzer for access by a pipettor or the like of the analyzer. The analyzer transfers fluid from a first vial on the variable reagent rack and at least one fluid from the common reagent pack into a reaction vessel containing a first patient sample. The analyzer then transfers fluid from a second vial on the variable reagent rack, the reagent in the second vial being different from the reagent in the first vial, and at least one fluid from the common reagent pack into a different reaction vessel containing a second patient sample.

BRIEF DESCRIPTION OF THE DRAWINGS

FIG. 4 is a schematic illustration of a vial retained in the variable reagent rack of FIG. 1;

FIG. 5 is a schematic illustration of a vial being removed from or inserted into the variable reagent rack of FIG. 1;

DETAILED DESCRIPTION OF THE PREFERRED EMBODIMENTS

Figure 1:
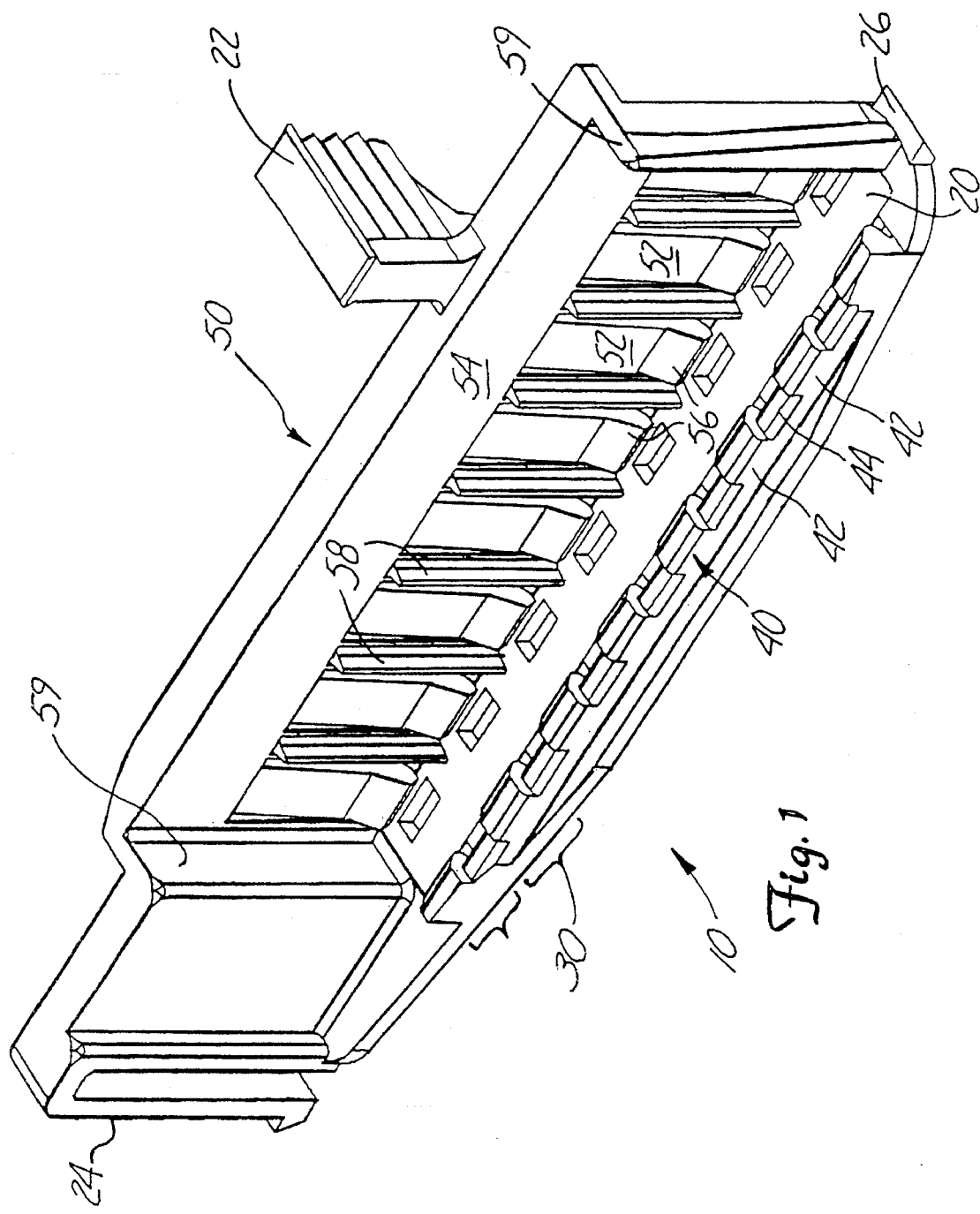
FIG. 1 is a perspective elevation view of a variable reagent rack in accordance with the present invention.

One embodiment of a variable reagent rack of the invention is illustrated in FIG. 1. As can be seen from that drawing, this rack 10 comprises a base 20 and a series of vial-receiving stations 30 spaced along at least a portion of the base. The precise shape and size of the base are not critical to the invention; the base is optimally designed to allow the vials to be supported on the rack 10 and to permit the filled rack to be used in a space designed for a standard-shaped reagent pack on the analyzer with which it is to be used.

The rack 10 of FIG. 1 includes a first wall 40 and a second wall 50. These walls are desirably generally parallel so that the space between the walls does not vary along the length of the rack, providing vial stations 30 all having the same width. The first wall 40 includes a series of abutments 42 spaced along its length, with one abutment being associated with each vial station 30. As described below in connection with FIGS. 4 and 5, these abutments 42 include shoulders 46 (best seen in those FIGS. 4 and 5) extending inwardly toward the second wall 50 to help hold a vial in place on the rack. In the embodiment shown, these abutments are spaced from one another by straight wall segments 44. If the shape of the vials to be used with the rack would so permit, the abutments could be continuous, presenting an elongate, uninterrupted abutting wall; in the preferred embodiment of the invention employing the vial 60 illustrated in FIGS. 2–5, though, the abutments must be spaced from one another as shown.

The second wall 50 includes a series of clips 52 spaced along its length, with one clip being associated with each vial station 30. These clips 52 are formed of a resilient material, such as an organic plastic, to permit them to move to permit vials to be placed onto and removed from the rack, as detailed below. Whereas the abutments 42 of the first wall could abut one another to present a solid wall, the clips 52 of the second wall should remain discrete so that they may flex independently of one another to permit insertion and removal of individual vials without loosening the grip of other clips on vials in other vessel stations 30.

The clips are biased toward the position shown in FIG. 1, wherein they extend inwardly of the rest of the second wall, i.e. toward the first wall 40. This biasing can be accomplished in any useful fashion. The clips 52 may take the form of an elongate leaf spring, as shown, or a separate biasing spring or other suitable mechanism may be used. The leaf spring can extend downwardly from an upper portion 54 of the wall 50, but this need not be the case. For example, the clips could instead be attached to the base 20 and extend upwardly therefrom. The free end of each clip defines an abutting shoulder 56 which, as explained below in connection with FIG. 4, helps retain vials in their respective vial stations 30.

Figure 2:
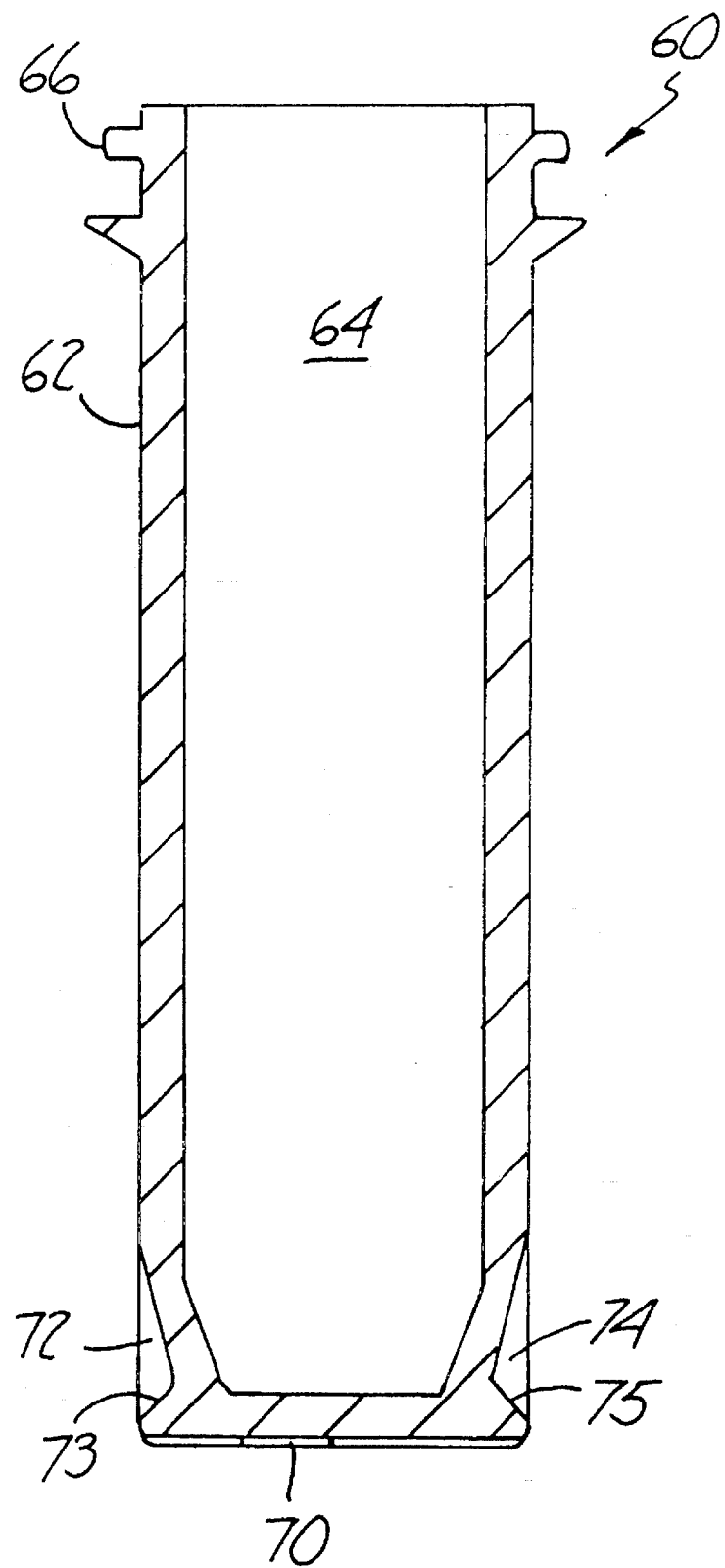
FIG. 2 is a side, cross sectional view of a vial for use with the variable reagent rack of FIG. 1.
Figure 3:
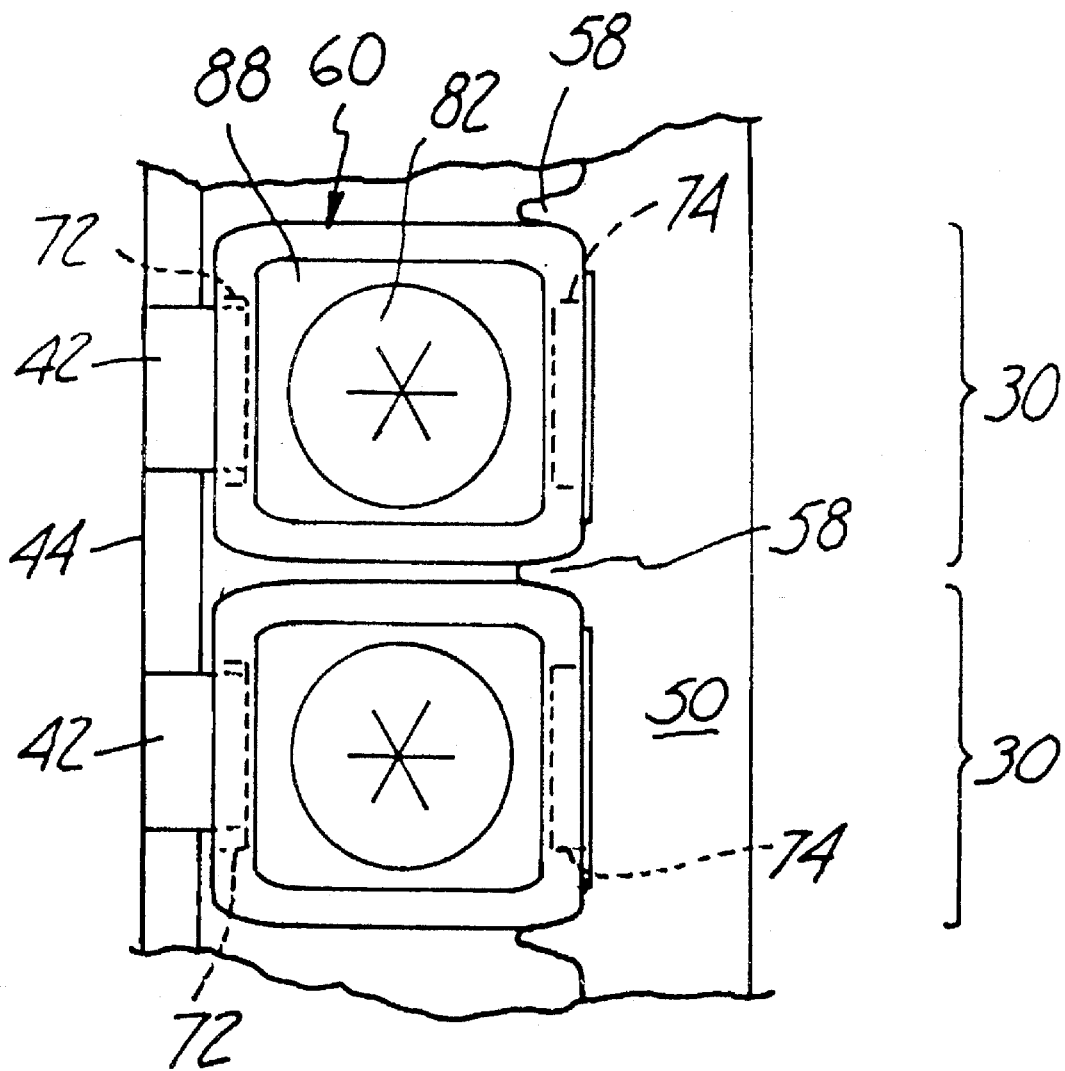
FIG. 3 is a top view of two vials such as the vial of FIG. 2 in a portion of the rack of FIG. 1.

Depending on the shape of the vial to be used in the rack 10, there may be little or no clearance between vials at adjacent vial stations 30. The vials shown in FIGS. 2–5 and the rack shown in FIG. 1, though, are shaped to permit some clearance between adjacent vials to simplify removal and insertion of vials. If the vials are spaced from one another, one of the two walls may include inwardly extending fingers 58 between adjacent vial stations 30. These fingers desirably extend vertically along the wall and serve to vertically support the vials in the vial stations (as shown in FIG. 3) to prevent them from being knocked from side to side during use. In the preferred embodiment shown in the drawings, the fingers 58 are included on the second wall 50 to simplify removal and insertion of vials. At the outer ends of the outermost vial stations 30, a more solid end wall 59 can be provided instead of another finger. Since these end walls will be positioned adjacent the ends of the rack, they will not greatly interfere with handling of the vials.

The rack 10 can also include a manually graspable handle 22 or the like to allow the operator to more readily add the rack onto or lift the rack off of a reagent platform (not shown). In the embodiment illustrated in FIG. 1, the variable reagent rack 10 is also provided with a forward tab 24 and a rearward tab 26. Tabs such as these may be used to properly orient and position the rack on a reagent platform within an automated analyzer. The tabs may also serve to releasably secure the rack to the platform to prevent unwanted movement of the rack during use, helping to ensure that the reagent rack is properly situated for access by a pipetting probe. It is to be understood that the shape and location of these tabs, as well as the overall size and shape of the rack, may be varied for use in automated analyzers having different configurations without departing from the scope of the present invention.

The exact configuration of the vials used with a rack of the invention can be varied as needed to provide the desired reagent volume and other factors. FIG. 2 shows a vial suitable for use in conjunction with the specific rack 10 shown in FIG. 1. The vial 60 includes an upwardly extending wall 62 which, together with the floor 70 of the vial, defines an inner cavity 64 for receiving a quantity of a reagent. If so desired, the wall 62 may taper inwardly adjacent the floor of the vial, as shown, to help ensure that the pipettor accessing the vial can withdraw substantially all of the reagent in the vial to avoid needlessly wasting reagent. The cavity 64 is desirably large enough to provide sufficient reagent to conduct a plurality of assays to avoid having to replace the vial after a single use. As explained in more detail below in connection with FIGS. 4 and 5, the vials also include a pair of recesses 72, 74 adjacent the floor 70. These recesses are sized and shaped to receive an abutment 42 and a shoulder 56 of a clip, respectively, of the rack 10.

As best seen in FIGS. 3–5, the vial 60 desirably also includes cap across its top to prevent evaporation of the reagent. This cap 80 includes a self-resealing inner seal 82 through which a pipettor (not shown) will pass to access the reagent within the vial. This inner seal may be formed of a resilient polymeric material which will allow the pipettor to pass through the membrane yet substantially reseal itself when the needle of the pipettor is withdrawn. The inner seal should retain this self-sealing capability through a number of cycles to minimize evaporation between the withdrawal of reagent for the first assay and the withdrawal of reagent for the last assay for the reagent in the vial.

For example, the inner seal 82 may have a composite structure comprising a thicker ply of a fairly soft, resilient polymeric material disposed between thinner reinforcing plies of a more rigid polymeric sheet material. The resilient ply can include tabs cut therethrough to define an entrance for a pipettor (which may yield an asterisk-like cut in the resilient ply such as is shown in FIG. 3). The reinforcing plies may include ports large enough to be spaced about the outer edge of the tabs, helping to reinforce the inner seal against strain associated with friction with the pipettor while still permitting the tabs to be deflected by the pipettor and resiliently return to an abutting, sealing relationship with one another. Self-resealing closures are known in the art and need not be discussed in any further detail here; the exact seal selected is not critical to the present invention and any suitable seal can be used.

The cap 80 also includes an overcap 84 which keeps the inner seal 82 in sealing contact with the upper edge of the wall 62 of the vial. In the embodiment shown, the overcap 84 includes a peripheral wall 86 which extends downwardly along a portion of the vial wall and may include a tab for locking against an outwardly extending flange 66 attached to the vial wall. The overcap also includes an inner rim 88 which engages the periphery of the inner seal and urges the inner seal against the upper edge of the wall 62. The overcap should not extend over the central axis of the vial, but instead should be spaced away from that axis to permit the pipettor free access to the inner seal during use.

FIG. 3 shows a top view of two of the vials 60 in two adjacent vessel stations 30 of a rack. In this embodiment, the vials are generally square in cross section, but the vials could instead be generally cylindrical or any other desired shape.

The recesses 72, 74 of the vessels can comprise generally parallel slots extending along the length of their respective opposed walls of the vial. In the embodiment depicted, though, the recess does not extend along the length of the entire vial wall, but instead extends only along a portion of the walls to define a recess only slightly wider than the abutment 42 or the shoulder 56 of the clip to be received in the recess (72 and 74, respectively). This will help center the vial in its station 30 to ensure consistent positioning of the vial for access by an automated pipettor.

FIG. 3 also illustrates the advantages of providing fingers 58 on the rack. These fingers are adapted to engage the wall of each vial adjacent its corners and extend inwardly between the vials for a short distance. This serves to vertically support the vials and separate one vial from another, as well as assist in the consistent positioning of the vials for access by the pipettor.

The vials may include positive identification of the vial to help the analyzer automatically track the vial. For example, a bar code label (not shown) may be attached to the wall of the vial. This positive identification of the vial can be used to inform the analyzer what reagent is in the vial and, if so desired, each time a quantity of the reagent is withdrawn from the vial the analyzer can record the withdrawal so that it can automatically track how much reagent remains in the vial and how many more assays can be conducted with the remaining reagent. Such identification and tracking systems are well known in the art and need not be detailed here.

FIG. 4 shows a vial 60 retained in a vial station 30 of the rack 10 and FIG. 5 illustrates how the vial can be inserted into or retracted from the rack. Turning first to FIG. 4, the floor 70 of the vial 60 is positioned adjacent the base 20 of the rack and desirably rests against the base. The vial is substantially vertical, with the wall 62 of the vial being immediately adjacent the second wall 50 of the rack. The vial desirably extends upwardly above the top of the second wall, permitting an operator to easily grasp an upper portion of the vial when removing the vial from the rack.

One of the abutments 42 of the first wall 40 is received in the recess 72 on one side of the vial and the abutment desirably engages the angled bottom face 73 of that recess. Similarly, a shoulder 56 of a clip 52 of the second wall is received in the other recess 74 and engages the bottom face 75 of that recess. The positioning of the abutment 42 and shoulder 56 in their respective recesses 72, 74 will help keep the vial on the rack 10 as the rack is handled by an operator or moved within the analyzer.

The arrangement of the abutment in the recess 72 of the present rack 10 and the presence of the wall 50 will tend to strongly grip the vial and prevent it from becoming dislodged from its vial station when the vial is drawn upwardly. For example, when a pipettor is withdrawn from the vial through the inner seal 82 of the cap 80, it will tend to pull directly upwardly on the vial. This can be attributed to the fact that the abutment 42 extends into the recess 72 farther than the distance between the floor 70 of the vial and the adjacent bottom portion of the second wall 50. The distance which the abutment extends into the recess 72 is designated in FIG. 4 as distance "A" while the shorter distance "B" refers to the space between the floor 70 of the vial and the bottom of the second wall. The distance A should be greater than the distance B, and is desirably significantly greater than the distance B. In a particularly preferred embodiment, the distance A is at least three times the distance B.

Having the abutment 42 extend farther into the recess 72 than the distance between the wall 62 of the vial and the second wall 52 will effectively prevent the vial from being removed when it is lifted generally vertically. The floor of the vial becomes pinned between the bottom face 43 of the abutment and the vial can only be extracted by moving it away from the abutment and toward the second wall 50. If the space between the second wall and the vial is less than the distance the abutment extends into the recess 72, the vial cannot be lifted vertically out of engagement with the abutment. In order to lift the vial off of the rack only by urging it upwardly, one must use enough force to deform the floor of the vial enough to clear the abutment. If the distance A is at least three times the distance B in FIG. 4, the force needed to deform the vial sufficiently to permit its vertical removal will be much greater than that a properly operating pipettor would likely ever exert on the vial, ensuring that the vial remains in the rack during use.

One of the primary purposes of the shoulder 56 of the clip 52 is to help keep the vial from being accidentally tipped to the side during handling or use. However, the orientation of the clip 52 can further enhance the grip on the vials as the pipettor is withdrawn.

As the withdrawing pipettor pulls upwardly on the vial, the bottom face 75 of the recess 74 will tend to urge upwardly against the shoulder 56 of the clip. As the clip is a leaf spring which hinges generally about a line in a plane with the rest of the second wall 50, upward force on the shoulder 56, which extends inwardly toward the vial, will tend to draw the shoulder further inwardly, only enhancing the engagement between the shoulder and the recess 74. This enhances the connection between the individual vials 60 and the rack 10. It should be understood, though, that this is essentially a side benefit of the clip of this invention and that the spacing of the abutment and the second wall 50 described above will, in most instances, be sufficient to prevent the pipettor from inadvertently dislodging the vials during use.

When an operator desires to remove a vial from the rack, the operator must tilt the vial in a direction away from the second wall 50, as shown in FIG. 5. If one were to simply pull directly up on the vial, the shoulder 56 would only more strongly engage the vial, as noted above. However, by first tilting the vial, the recess 74 can act against the shoulder 56 to urge the clip 52 against its biasing force outwardly away from the first wall 40. The shoulder will tend to slide along the bottom face 75 of the recess 74 until it clears the recess, freeing that side of the vial from the rack. The vial can then be further pivoted until the abutment 42 of the first wall clears the bottom wall 73 of the recess 72, whereupon the vial can be removed from its station on the rack.

A new vial can be added onto the rack in much the reverse of this process. In particular, the vial is optimally inserted at an angle such that the floor 70 of the vial engages the clip 52 of the second wall. While pushing against the clip, the abutment 42 can be positioned in the recess 72 of the vial to lock in that side of the vial. The vial can then be brought generally vertical. In so doing, the clip will be depressed until it clears the floor 70 of the vial and can slip into the recess 74 provided for it. This will position the vial within the rack substantially as shown in FIG. 4.

Figure 6:
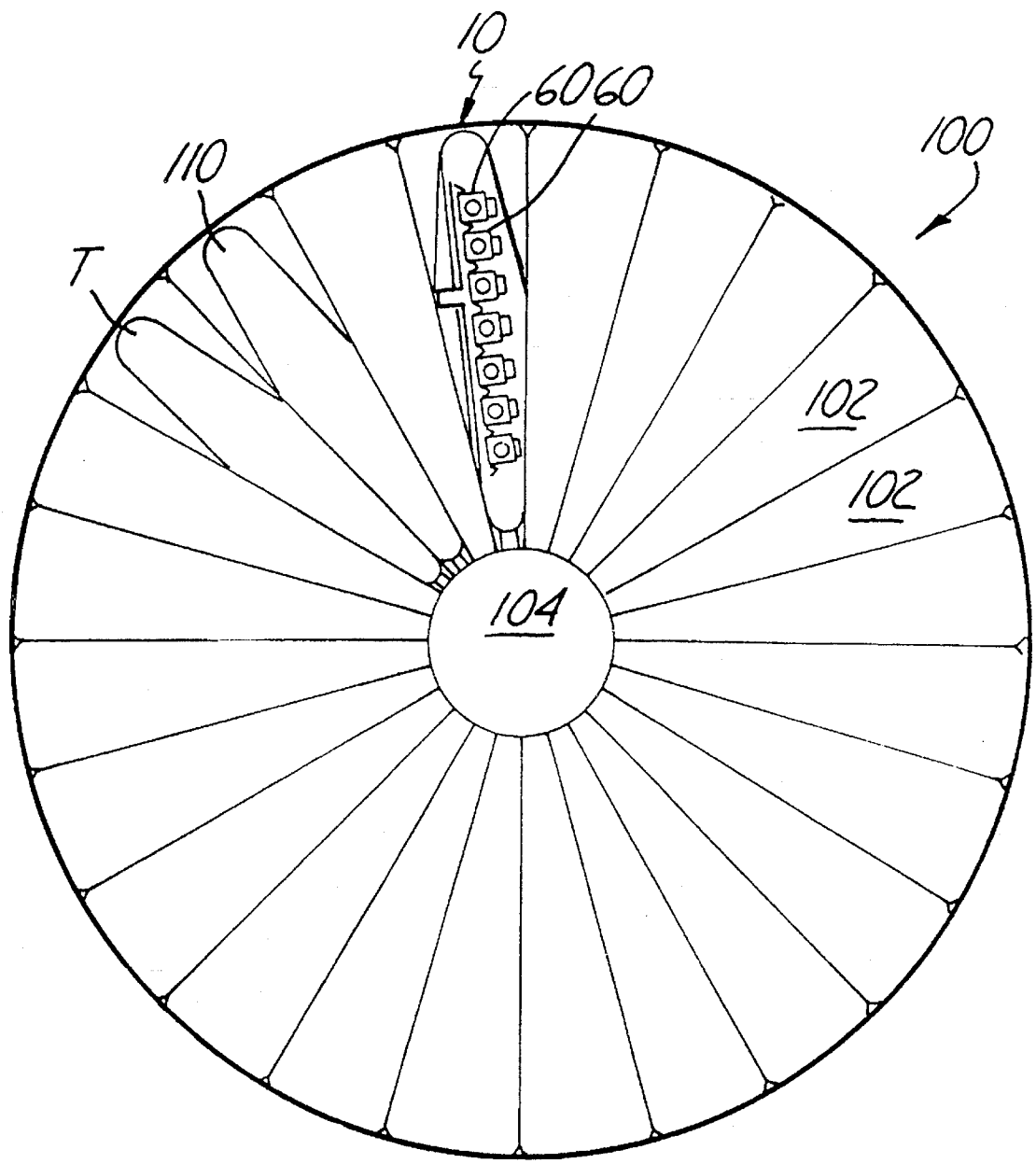
FIG. 6 is a schematic illustration of a reagent carousel in accordance with the invention containing variable reagent racks and common reagent packs on a common platform.

In accordance with a further embodiment of the invention, a reagent supply system includes a variable reagent rack 10 and a common reagent pack on a reagent supply platform. A schematic illustration of this embodiment of the invention is shown in FIG. 6. The reagent supply platform 100 can be positioned within an analyzer and desirably includes a series of uniformly shaped ports 102 for receiving reagent packs for use with the analyzer. The platform 100 and the ports 102 can be of any shape suitable for use in a particular analyzer, but the illustrated embodiment comprises a generally circular platform having a series of generally wedge-shaped ports 102 extending radially outwardly from a hub 104 of the platform.

In this embodiment, the reagent packs and the rack of the invention are desirably generally wedge shaped, having a tapering forward end which is received adjacent the hub. The packs need not taper along their entire length, though; the embodiment of the variable reagent rack 10 shown in FIG. 1, for example, tapers adjacent its forward end (adjacent the forward tab 24) but reaches its maximum width well short of the rearward end (adjacent the rearward tab 26). The reagent platform 100 desirably includes mating recesses (not shown) for receiving the forward and rearward tabs of the rack and similar projections on the common reagent packs.

Figure 7A:
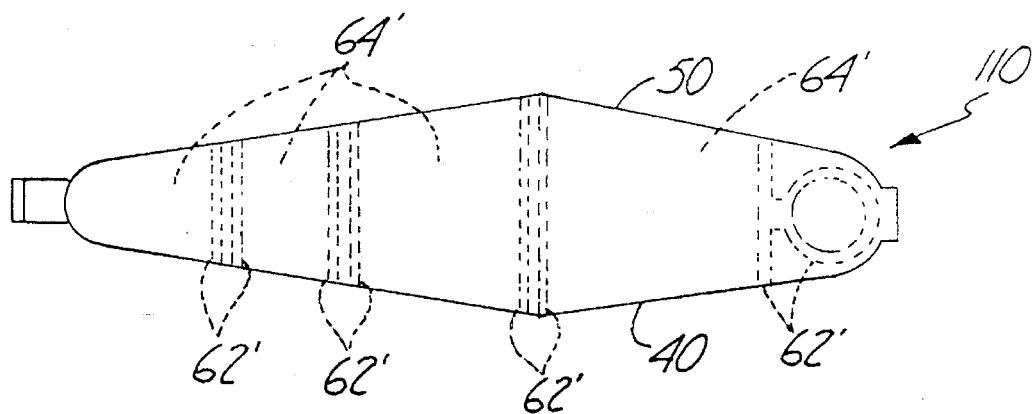
FIGS. 7A and 7B are top and side views, respectively, of one embodiment of a common reagent pack for use with the present invention.
Figure 7B:
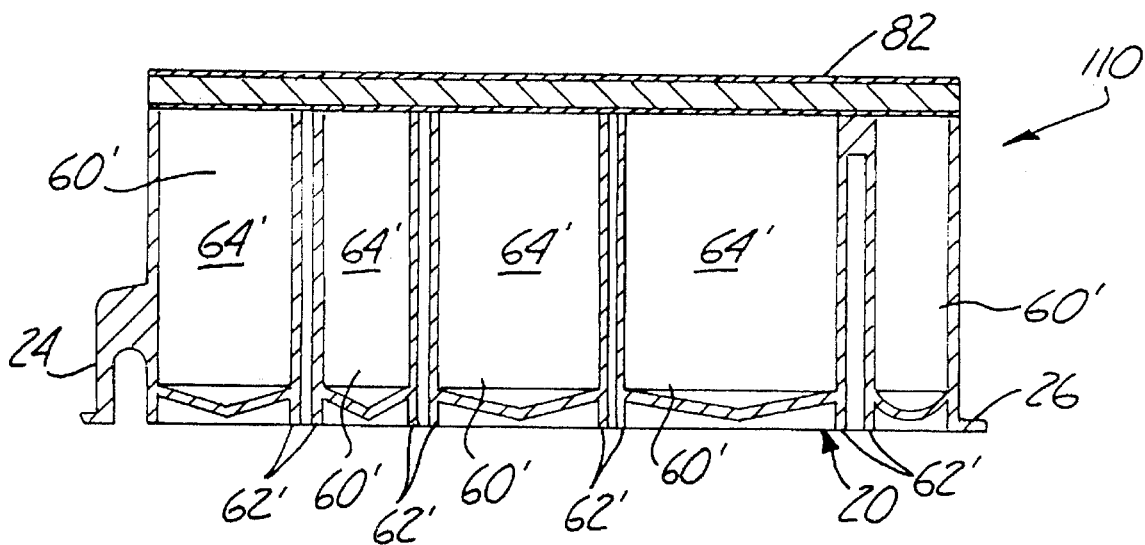

A schematic cross sectional view of a common reagent pack 110 of this embodiment of the invention is shown in FIGS. 7A and 7B, wherein elements performing similar functions to elements of FIG. 1 bear like reference numerals. The pack 110 includes a pair of opposed, upstanding walls 40, 50 extending along opposite sides of the pack and upwardly from a base 20 of the pack. Whereas the base 20 of the rack 10 is generally flat and continuous, the base of the common reagent pack 110 may be broken into discrete segments by the walls 62' of the reagent wells 60'.

These reagent wells 60' provide a series of separate cavities 64' for receiving different reagents and the number of wells and the volumes of reagents they are capable of holding can be varied widely depending on the number of common reagents needed and the relative volumes of those reagents needed to run an assay. For example, the common reagent pack may include just three wells, with one well holding magnetic particles or the like, another holding a conjugate for the assay and the third containing a standard solution for calibration of the analyzer with the pack. This combination of reagents and the number of wells can be varied readily to meet different parameters of the analyzer in which the pack is used and the specific assays to be performed.

Turning back to FIG. 6, the reagent supply system of the invention includes at least one variable reagent rack 10 of the invention and at least one common reagent pack 110 on the reagent platform 100 at one time. This permits the pipettor (not shown) to access both the rack, which contains a plurality of interchangeable vials holding different assay-specific reagents, and the common reagent pack, which includes all of the reagents common to all of the assays performed using the reagents in the vials. As explained below in connection with the method of the invention, this enhances flexibility of the system without occupying unneeded spaced on the reagent platform in the analyzer.

As noted above, another embodiment of the present invention comprises a method for supplying reagents to reaction vials for conducting a series of different assays. In accordance with this method, the types of assays to be performed on one or more patient samples will be determined. In some instances, this may be accomplished in an automated fashion, such as by having all samples bar-coded and cross-referenced to indicate which assays are to be performed for that sample. More commonly, though, this information will need to be determined by the operator and entered into the analyzer when the sample is added to the analyzer for processing. Once the specific assays to be performed are determined, the operator will need to ensure that the reagents necessary to perform the assays are on the reagent supply system. If sufficient quantities of all of the necessary reagents are not already on the supply system, the operator will need to add them to the system.

In current practice, this may simply require the operator to place a single, test-specific reagent pack onto the supply system. However, in using the reagent supply system of the invention, reagents for more than two types of assay can be provided on just two ports 102 of the reagent platform by using the variable reagent rack 10. In using such a reagent pack, an operator will determine how many of a plurality of requested assays can be performed using a common pack of reagents. The operator can then load a series of vials 60 containing different assay-specific reagents onto a variable reagent rack 10 of the invention. Then both the common reagent pack 110 and the loaded rack 10 can be positioned on the reagent platform for access by the analyzer.

It should be understood that this step of positioning the common reagent pack 110 and the rack 110 on the reagent platform may not require the operator to physically add the common reagent pack onto the platform 100. For example, a common reagent pack having sufficient quantities of the common reagents to perform the required assays may already be on the platform. The important aspect of this step of the present method is that the operator place at least one loaded reagent rack 10 onto the system so that both the rack and a suitable common reagent pack 110 be positioned on the system at the same time for access by the analyzer.

For example, if a patient sample is delivered for analysis with a request for a series of allergen assays to determine the nature of a patient's allergies, all of the reagents for that series of allergen assays may be the same, with only the specific allergen varying from one assay to the next. In such a situation, the operator can select a series of vials 60, with each vial containing a different allergen necessary for one of the requested assays. In part due to the presence of the supporting fingers 58 of the rack 10, one need not load every vial station 30 on the rack in order to use the rack in an analyzer. If only three different allergen assays are requested, only three vials need be loaded onto stations 30 of the rack 10; if more vials are needed than can fit on one rack, more than one rack can be loaded. The loaded rack(s) are placed on the reagent platform 100 and, if a common reagent pack having sufficient reagents is not already loaded onto the platform, the operator can also add such a pack 110 onto on the system.

The analyzer will then process the sample or samples in accordance with its own standard protocol. Protocols of analyzers differ widely, but the basic method of the invention will not depend on the specific protocol used by the analyzer. In processing patient samples in accordance with the present method, the analyzer will access a first vial 60 on the variable reagent rack 10 and withdraw a quantity of a first reagent in that vial and dispense that reagent into a reaction vessel (not shown in the drawings) containing a quantity of the patient sample. The analyzer will also access a common reagent pack 110 and transfer a quantity of at least one reagent fluid from that pack into the same reaction vessel. The order of the addition of patient sample, variable reagent from a specific vial and the common reagent(s) can be varied in accordance with the analyzer's standard protocol; there is no need to add them in any specific order to perform the present method.

In a preferred embodiment, the analyzer will then access a second vial 60 containing a second reagent on the same reagent pack 10, the second reagent being different from the first reagent contained in the first vial. The analyzer will transfer a quantity of the second reagent from the second vial into a second reaction vessel (not shown in the drawings). The analyzer can then return to the same common reagent pack 110 and withdraw a quantity of the same common reagent(s) removed from the pack 110 in the previous step and dispense the common reagent(s) into the second reaction vessel.

Accessing the vials and the common reagent pack and transferring the reagents to the reaction vessel can be performed in whatever fashion the analyzer normally transfers reagents. For example, a pipettor may be moveable between a pipetting station for accessing the reagent supply system and a reagent addition station where the reagents are dispensed into reaction vessels. If the pipetting station is stationary with respect to the rest of the analyzer, the platform 100 of the reagent supply system may be moveable to position the desired reagent pack 110 or vial rack 10 at the pipetting station for access by the pipettor.

By way of example, the present method will be explained in connection with conducting a series of assays to determine allergenic reactions of a patient's sample. As noted above, this may occur by having a patient sample delivered for a series of allergen-specific assays. In conducting such a series of allergen tests, it may also be desirable to test the total level of immunoglobulin E (IgE) in a patient's sample—if the total IgE in the sample falls below a certain concentration, it is unlikely that the patient has any significant allergies and, if so desired, the allergen-specific tests then need not be conducted because it is unlikely that they will turn up any positive results.

In conducting such a series of allergenic assays, any suitable assay format me be utilized. In one preferred embodiment, the assays are conducted using paramagnetic particles, haptenated liquid allergens and a chemiluminescent detection step. In such an assay, each of the vials 60 on a rack 10 will contain a specific haptenated allergen such as a haptenated Lol p I or Amb a I, or a haptenated anti-IgE complex. Haptenated allergens and anti-IgE complexes are well known in the art, as are methods of isolating and making these antigens, and therefore need not be discussed in detail here. The common reagent pack 110 will include a solution containing suitable paramagnetic particles, which may bear anti-hapten on their surfaces, in one well 60' and an enzyme labeled conjugate in another of the wells 60'.

When the tests are to be conducted, an operator can determine the series of allergen-specific assays to be conducted and select vials containing the appropriate haptenated allergen and load these selected vials onto stations 30 of the rack 10. The operator can also select a separate vial containing anti-IgE and load that vial onto the rack as well, or the anti-IgE can be contained in a separate reagent pack (T in FIG. 6) dedicated to total IgE assays, which can remain on the reagent supply platform 100 if so desired. Once all of the appropriate vials have been loaded onto the rack, the operator can place the loaded rack in a port 102 on the reagent supply platform 100. If a common reagent pack 110 for allergen assays is not already present on the reagent supply platform, the operator can add such a pack 110 to the platform as well.

Once the rack and the reagent pack are so positioned on the reagent supply platform, the analyzer will schedule and process the assays in accordance with its ordinary processing protocol. When the first in the series of assays is to be performed, the analyzer will access the vial containing a first haptenated allergen reagent or anti-IgE reagent on the rack 10 and transfer a quantity of the allergen reagent to a reaction vessel and will transfer a quantity of the paramagnetic particles from the common reagent pack to the reaction vessel as well. The system will also transfer a quantity of the patient's sample to the same reaction vessel and the vessel will be incubated. After an appropriate time, the sample will be washed and the analyzer will then transfer a quantity of the enzyme labeled conjugate from the common reagent pack to the reaction vessel. After a further incubation, a chemiluminescent substrate sensitive to the enzyme in the labelled conjugate can be added, which will generate a luminescent signal detectable by the analyzer to generate a test result in a known fashion.

Once the analyzer has transferred a quantity of the patient sample, the first haptenated allergen (or anti-IgE) and the paramagnetic particles to the first reaction vessel and it begins incubation, the analyzer can begin a second allergen-specific assay for a different allergen. This is accomplished in much the same fashion as the first allergen, with the analyzer transferring a quantity of a second haptenated allergen from a second vial on the same rack and a quantity of the paramagnetic particle solution from the same common reagent pack to a second reaction vessel for incubation. After incubation and a first wash, the analyzer can transfer a quantity of the conjugate from the same common reagent pack and incubate, wash add the substrate and read the luminescence as before.

This process can then be repeated as necessary until all of the requested allergen-specific assays have been conducted. Alternatively the first assay conducted may measure total IgE using an anti-IgE reagent as noted above. If the results of this assay indicate that the total IgE level falls below a certain threshold this can be reported to the operator or a signal can be sent to the analyzer's controller and, if so desired, the series of assays can be terminated on the assumption that the allergen-specific assays are not likely to e necessary.

While a preferred embodiment of the present invention has been described, it should be understood that various changes, adaptations and modifications may be made therein without departing from the spirit of the invention and the scope of the appended claims.

What is claimed is:

1. A reagent supply system for an automated analyzer comprising a reagent rack for releasably retaining a plurality of vials, and at least one of said vials having first and second recesses, the rack comprising a base, a first wall extending upwardly from the base and a second wall extending upwardly from the base, the first and second walls being substantially parallel to one another, the first wall including a substantially rigid abutment extending inwardly toward the second wall and adapted to engage said first recess, the second wall including a flexible clip having a shoulder thereon, the shoulder being moveable away from the first wall and being biased toward a position adapted to engage said second recess on said vial.

2. The reagent supply system of claim 1 wherein the vial has a floor and a wall extending generally upwardly therefrom, the floor and wall together defining a reagent-holding cavity of the vial, said first and second recesses of the vial comprising recessed portions of said wall.

3. The reagent supply system of claim 1 wherein each of said recesses include a bottom face, the abutment being adapted to abut the bottom face of the first recess and the shoulder being adapted to abut the bottom face of the second recess.

4. The reagent supply system of claim 2 wherein the abutment is in engagement with the first recess and the shoulder is in engagement with the second recess to releasably retain the vial on the rack, the shoulder being spaced inwardly of the rest of the second wall.

5. The reagent supply system of claim 1 wherein the first wall comprises a plurality of abutments and the second wall comprises a plurality of clips, one abutment, one clip and a length of the base together defining a vial-receiving station of the rack.

6. The reagent supply system of claim 5 further comprising an elongate, generally vertical support finger disposed between adjacent vial-receiving stations, the finger being adapted to vertically support a vial received in each of said adjacent vial-receiving stations.

7. The reagent supply system of claim 1 further comprising a common reagent pack and a reagent supply platform, the platform being adapted to support and releasably retain at least one variable reagent rack and at least one common reagent pack for access by the automated analyzer, the common reagent pack having a plurality of common reagents contained therein.

8. The reagent supply system of claim 7 wherein each of the vials contains a different reagent adapted to coact with the common reagents on the common reagent pack to perform a specific assay on the analyzer.

9. The reagent supply system of claim 8 wherein the platform comprises a plurality of ports shaped to receive and retain reagent packs, the at least one variable reagent rack and the at least one common reagent pack being shaped to be releasably received within one of said ports.

10. A reagent supply system for an automated analyzer comprising:
   a. at least one vial comprising a floor and a wall extending generally upwardly therefrom, the floor and wall together defining a cavity of the vial, recessed portions of said wall defining first and second recesses of the vial; and
   b. a reagent rack comprising a base and first and second walls extending upwardly from the base, the floor of the vial being disposed adjacent the base; the first wall including a bottom portion and an abutment extending inwardly toward the second wall a distance "A" beyond the bottom portion, the abutment engaging the first recess on the vial; the second wall including a bottom portion and a flexible clip having a shoulder thereon, the shoulder being moveable away from the first wall and being biased toward engagement with the second recess on said vial, the floor of the vial being spaced a distance "B" from the bottom portion of the second wall, the distance "A" being greater than the distance "B".

11. The reagent supply system of claim 10 wherein the distance "A" is at least three times the distance "B".

12. The reagent supply system of claim 11 wherein each of said recesses include a bottom face, the abutment being adapted to abut the bottom face of the first recess and the shoulder being adapted to abut the bottom face of the second recess.

13. The reagent supply system of claim 10 wherein the rack is adapted to releasably retain a plurality of vials, the first wall comprising a plurality of abutments and the second wall comprising a plurality of clips, one abutment, one clip and a length of the base together defining a vial-receiving station of the rack.

14. The reagent supply system of claim 13 further comprising an elongate, generally vertical support finger disposed between adjacent vial-receiving stations, the finger being adapted to vertically support a vial received in each of said adjacent vial-receiving stations.

15. The reagent supply system of claim 10 wherein the clip depends downwardly from an upper portion of the second wall, the shoulder extending inwardly from said upper portion such that urging the vial generally vertically upwardly draws the shoulder further inwardly toward the second recess.

* * * * *